US012667805B2

(12) United States Patent
Valentin et al.

(10) Patent No.: US 12,667,805 B2
(45) Date of Patent: Jun. 30, 2026

(54) FACILITY AND METHOD FOR PRODUCING BIOMETHANE WITH LIMITED METHANE LOSS AND LIMITED CO₂ EMISSIONS

(71) Applicant: L'Air Liquide, Société Anonyme pour l'Etude et l'Exploitation des Procédés Georges Claude, Paris (FR)

(72) Inventors: Solène Valentin, Voreppe (FR); François Barraud, Shanghai (CN)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 639 days.

(21) Appl. No.: 17/924,559

(22) PCT Filed: May 4, 2021

(86) PCT No.: PCT/EP2021/061656
§ 371 (c)(1),
(2) Date: Nov. 10, 2022

(87) PCT Pub. No.: WO2021/228616
PCT Pub. Date: Nov. 18, 2021

(65) Prior Publication Data
US 2023/0338889 A1      Oct. 26, 2023

(30) Foreign Application Priority Data
May 13, 2020      (FR) ...................................... 2004692

(51) Int. Cl.
| | |
|---|---|
| *B01D 53/22* | (2006.01) |
| *B01D 3/14* | (2006.01) |
| *B01D 53/00* | (2006.01) |
| *B01D 53/30* | (2006.01) |
| *C07C 7/00* | (2006.01) |
| *C07C 7/04* | (2006.01) |
| *C07C 7/144* | (2006.01) |
| *C10L 3/10* | (2006.01) |
| *F25J 3/02* | (2006.01) |

(52) U.S. Cl.
CPC ........... *B01D 53/226* (2013.01); *B01D 3/145* (2013.01); *B01D 3/148* (2013.01); *B01D 53/002* (2013.01); *B01D 53/229* (2013.01); *B01D 53/30* (2013.01); *C07C 7/005* (2013.01); *C07C 7/04* (2013.01); *C07C 7/144* (2013.01); *C10L 3/104* (2013.01); *F25J 3/0233* (2013.01); *B01D 2256/245* (2013.01); *B01D 2257/304* (2013.01); *B01D 2257/504* (2013.01); *B01D 2257/708* (2013.01); *B01D 2257/80* (2013.01); *B01D 2258/05* (2013.01); *C10L 2200/0469* (2013.01);
(Continued)

(58) Field of Classification Search
CPC ...... B01D 53/226; B01D 3/145; B01D 3/148; B01D 53/002; B01D 53/229; B01D 53/30; B01D 2256/245; B01D 2257/304; B01D 2257/504; B01D 2257/708; B01D 2257/80; B01D 2258/05; C07C 7/005; C07C 7/04; C07C 7/144; C10L 3/104; C10L 2200/0469; C10L 2290/543; C10L 2290/548; C10L 3/101; C10L 3/103; C10L 3/106; C10L 2290/10; C10L 2290/30; C10L 3/12; F25J 3/0233; F25J 2200/02; F25J 2205/40; F25J 2205/80; F25J 2210/66; F25J 2280/50; F25J 3/0209; F25J 3/0266; Y02C 20/40; Y02E 50/30; Y02P 20/59; C12M 47/18
See application file for complete search history.

(56) References Cited

U.S. PATENT DOCUMENTS

| | | | | |
|---|---|---|---|---|
| 4,085,192 A | * | 4/1978 | Van Scoy ............. | C01B 17/167 95/183 |
| 5,082,534 A | * | 1/1992 | Breu ....................... | C10B 49/04 202/241 |

(Continued)

FOREIGN PATENT DOCUMENTS

| | | |
|---|---|---|
| EP | 3 632 525 | 4/2020 |
| WO | WO 2014 183977 | 11/2014 |

OTHER PUBLICATIONS

International Search Report for corresponding PCT/EP2021/061656, Sep. 1, 2021.

*Primary Examiner* — In Suk C Bullock
(74) *Attorney, Agent, or Firm* — Yan Jiang

(57) ABSTRACT

Disclosed are a facility and a method using the facility for treating a feed gas stream comprising at least methane and carbon dioxide by membrane permeation, the facility comprising: —a first membrane separation unit capable of receiving the feed gas stream and providing a first permeate and a first retentate, —a second membrane separation unit capable of receiving the first retentate and providing a second permeate and a second retentate, —a compressor for compressing the first permeate to a pressure of between 17 bar and 25 bar, —a means for cooling the first compressed permeate to a temperature lower than –40° C., —a distillation column for separating the first cooled permeate into a gas stream and a liquid stream, —at least one means for recycling the gas stream exiting the distillation column to the inlet of the first membrane separation unit, —a means for measuring the concentration of methane and/or carbon dioxide in the gas stream exiting the distillation column, —a means for comparing the concentration of methane and/or carbon dioxide measured by the measurement means with a target value, and —a means for adjusting the pressure and/or the temperature of the first permeate depending on the comparison carried out by the comparison means.

12 Claims, No Drawings

(52) U.S. Cl.
CPC ... *C10L 2290/543* (2013.01); *C10L 2290/548*
(2013.01); *F25J 2200/02* (2013.01); *F25J*
*2205/40* (2013.01); *F25J 2205/80* (2013.01);
*F25J 2210/66* (2013.01); *F25J 2280/50*
(2013.01)

(56)                    References Cited

U.S. PATENT DOCUMENTS

| | | | | |
|---|---|---|---|---|
| 9,108,894 | B1 * | 8/2015 | Foody ..................... | C10L 1/023 |
| 2012/0111051 | A1 * | 5/2012 | Kulkarni .............. | B01D 53/226 |
| | | | | 62/619 |
| 2017/0173520 | A1 * | 6/2017 | Acharya ............ | B01D 19/0068 |
| 2017/0327758 | A1 | 11/2017 | Tanaka et al. | |
| 2018/0280883 | A1 * | 10/2018 | Eda ...................... | B01D 53/229 |
| 2019/0321780 | A1 * | 10/2019 | Bikson ............... | B01D 53/0407 |

* cited by examiner

FACILITY AND METHOD FOR PRODUCING BIOMETHANE WITH LIMITED METHANE LOSS AND LIMITED CO$_2$ EMISSIONS

CROSS REFERENCE TO RELATED APPLICATIONS

This application is a 371 of International Application No. PCT/EP2021/061656, filed May 4, 2021, which claims priority to French Patent Application No. 2004692, filed May 13, 2020, the entire contents of which are incorporated herein by reference.

TECHNICAL FIELD

The present invention relates to a facility for the membrane permeation treatment of a gas stream containing at least methane and carbon dioxide to produce a methane-rich gas stream, and to a process using such a facility.

The invention relates in particular to the purification of biogas, for the purpose of producing biomethane in accordance with the specifications for injection into a natural gas network.

BACKGROUND

Biogas is the gas produced during the degradation of organic matter in the absence of oxygen (anaerobic fermentation), also known as methanization. This may be natural degradation—it is thus observed in marshland or in household waste landfills—but the production of biogas may also result from the methanization of waste in a dedicated reactor referred to as a methanizer or digester.

By virtue of its main constituents—methane and carbon dioxide—biogas is a powerful greenhouse gas; at the same time, it also constitutes a source of renewable energy which is appreciable in the context of the increasing scarcity of fossil fuels.

Biogas predominantly contains methane (CH$_4$) and carbon dioxide (CO$_2$) in proportions which can vary according to the way in which it is obtained, but also contains, in smaller proportions, water, nitrogen, hydrogen sulfide, oxygen, and also other organic compounds, in trace amounts.

Depending on the organic matter that has been degraded and on the techniques used, the proportions of the components differ, but on average biogas includes, on a dry gas basis, from 30% to 75% methane, from 15% to 60% CO$_2$, from 0 to 15% nitrogen, from 0 to 5% oxygen and trace compounds.

Biogas is put to profitable use in various ways. It may, after light treatment, be put to profitable use near the production site to provide heat, electricity or a mixture of both (cogeneration); the high carbon dioxide content reduces its calorific value, increases the costs of compression and transport and limits the economic benefit of this way of putting it to profitable use nearby.

Purifying biogas to a greater degree allows it to be put to broader use; in particular, extensive purification of biogas yields a biogas that has been purified to the specifications of natural gas and which can substitute for the latter; biogas thus purified is known as "biomethane". Biomethane thus supplements the natural gas resources with a renewable portion produced within the territories; it can be put to exactly the same uses as natural gas of fossil origin. It can be fed into a natural gas network or a vehicle filling station; it can also be liquefied to be stored in the form of liquefied natural gas (LNG), etc.

The ways in which biomethane is put to profitable use are determined according to the local context: local energy requirements, possibilities for putting it to profitable use as a biomethane fuel, and whether there is a natural gas transport or distribution network nearby, in particular. By creating synergy between the various parties operating in a given territory (farmers, manufacturers, civic authorities), the production of biomethane assists the territories in acquiring greater energy autonomy.

There are a number of steps that need to be completed between collecting the biogas and obtaining biomethane, the end-product that can be compressed or liquefied.

In particular, there are several steps needed prior to the treatment which is aimed at separating out the carbon dioxide in order to produce a stream of purified methane. A first step consists in compressing the biogas which has been produced and brought in at atmospheric pressure, and this compression can be obtained—in the conventional way—using a compressor. The following steps are aimed at stripping the biogas of the corrosive components, which are hydrogen sulfide and volatile organic compounds (VOCs); the technologies used are, conventionally, pressure swing adsorption (PSA) and trapping on activated carbon. Next comes the step which consists in separating out the carbon dioxide in order ultimately to furnish methane at the purity required for its subsequent use.

Carbon dioxide is a contaminant typically present in natural gas and it is common to need to remove it therefrom. Varying technologies are used to do this depending on the situation; among these, membrane technology is particularly efficient when the CO$_2$ content is high; and it is therefore used for separating out the CO$_2$ present in biogas originating from released gases or plant or animal waste digesters.

Membrane gas separation processes used for the purification of a gas, whether they use one or more membrane stages, have to make it possible to produce a gas at the required quality, for a low cost, while minimizing the losses of the gas which it is desired to upgrade. Thus, in the case of biogas purification, the separation performed is chiefly a CH$_4$/CO$_2$ separation which needs to allow the production of a gas containing, depending on its use, more than 85% CH$_4$, preferably more than 95% CH$_4$, more preferentially more than 97.5% CH$_4$, while minimizing the CH$_4$ losses in the residual gas and the cost of purification, the latter to a large extent being associated with the electricity consumption of the device that compresses the gas upstream of the membranes.

It is preferable for the plants that allow the production of a methane-enriched gas stream to be able to control the methane loss.

On that basis, one problem that arises is that of providing a facility that makes it possible to obtain a stream of biomethane at a constant concentration without any loss of its principal component, methane.

SUMMARY

One solution of the present invention is a facility for the membrane permeation treatment of a feed gas stream comprising at least methane and carbon dioxide, said facility comprising:
- a first membrane separation unit able to receive the feed gas stream and to supply a first permeate and a first retentate,
- a second membrane separation unit able to receive the first retentate and to supply a second permeate and a second retentate, a compressor for compressing the first permeate to a pressure of between 17 bar and 25 bar, a means for cooling the compressed first permeate to a temperature below −40° C., a distillation column for separating the cooled first permeate into a gas stream and a liquid stream, and at least one means for recycling the gas stream leaving the distillation column to the inlet of the first membrane separation unit.

Preferably, the means for recycling the gas stream leaving the distillation column comprises a set of valves and pipes.

DETAILED DESCRIPTION OF PREFERRED EMBODIMENTS

Depending on the case, the facility according to the invention may have one or more of the following features:

The facility comprises means for measuring the concentration of methane and/or carbon dioxide in the gas stream leaving the distillation column, means for comparing the concentration of methane and/or carbon dioxide measured by the measuring means with a target value, and means for adjusting the pressure and/or temperature of the first permeate as a function of the comparison made by the first comparing means.

The facility comprises a compressor for compressing the feed gas stream to a pressure of between 8 bar and 16 bar upstream of the first membrane separation unit.

The facility comprises an evaporator for evaporating the liquid stream leaving the distillation column.

The facility comprises a liquid tank for storing the liquid stream leaving the distillation column.

The facility comprises means for purifying the feed gas stream, placed upstream of the first membrane separation unit, and for at least partially removing an impurity chosen from water, hydrogen sulfide and volatile organic compounds.

The means for cooling the first compressed permeate to a temperature below −40° C. comprises a chiller and heat exchanger assembly.

A subject of the present invention is also a process for the membrane permeation treatment of a feed gas stream comprising at least methane and carbon dioxide, said process using the facility as defined above, and comprising:

a) A step of feeding the first membrane separation unit with the feed gas stream so as to produce a first retentate enriched in methane relative to the feed gas stream and a first permeate enriched in carbon dioxide relative to the feed gas stream, b) A step of feeding the first retentate to the second membrane separation unit so as to produce a second retentate enriched in methane relative to the first retentate and a second permeate enriched in carbon dioxide relative to the first retentate, c) A step of compressing the first permeate to a pressure of between 17 bar and 25 bar, d) A step of cooling the compressed first permeate to a temperature below −40° C., e) A step of separating the cooled first permeate into a gas stream and a liquid stream in the distillation column, and f) A step of recycling the gas stream leaving the distillation column to the inlet of the first membrane separation unit.

It should be noted that this recycling enables all the $CH_4$ contained in the gas stream to be recycled. Indeed, the gas stream leaving the distillation column will essentially comprise methane and the liquid stream leaving the distillation column will essentially comprise carbon dioxide.

The recycled portion in the feed gas stream will preferably be ⅓ of the feed gas stream.

Depending on the case, the process according to the invention may have one or more of the features below:

The process comprises a step of measuring the concentration of methane and/or carbon dioxide in the gas stream leaving the distillation column, a step of comparing the concentration of methane and/or carbon dioxide measured by the measuring means with a target value, and a step of adjusting the pressure and/or temperature of the first permeate as a function of the comparison made by the first comparing means. Preferably, the three steps are performed automatically by data transmission and data processing means. Preferably, the target value is between 10% $CH_4$ and 20% $CH_4$, The process comprises a step of compressing the feed gas stream to a pressure of between 8 bar and 16 bar upstream of the first membrane separation unit, The process comprises a step of evaporating the liquid stream leaving the distillation column.

The process comprises a step of storing the liquid stream leaving the distillation column in a liquid tank.

The process comprises a step of purifying the feed gas stream upstream of the first membrane separation unit so as to at least partially remove an impurity chosen from water, hydrogen sulfide and volatile organic compounds, the feed gas stream is biogas.

The solution proposed herein makes it possible to obtain a biomethane stream with a constant concentration without loss of its principal component, methane, but also makes it possible to avoid carbon dioxide emissions.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A facility for the membrane permeation treatment of a feed gas stream comprising at least methane and carbon dioxide, said facility comprising:

a first membrane separation unit able to receive the feed gas stream and to supply a first permeate and a first retentate;

a second membrane separation unit able to receive the first retentate and to supply a second permeate and a second retentate;

a compressor for compressing the first permeate to a pressure of between 17 bar and 25 bar;

a means for cooling the compressed first permeate to a temperature below −40° C.;

a distillation column for separating the cooled first permeate into a gas stream and a liquid stream;

at least one means for recycling the gas stream leaving the distillation column to the inlet of the first membrane separation unit;

a means for measuring the concentration of methane and/or carbon dioxide in the gas stream leaving the distillation column;

a means for comparing the concentration of methane and/or carbon dioxide measured by the measuring means with a target value, wherein the target value is between 10% $CH_4$ and 20% $CH_4$; and a means for adjusting the pressure and/or temperature of the first permeate as a function of the comparison made by the comparing means.

2. The facility as claimed in claim 1, wherein said facility comprises a compressor for compressing the feed gas stream to a pressure of between 8 bar and 16 bar upstream of the first membrane separation unit.

3. The facility as claimed in claim 1, further comprising an evaporator for evaporating the liquid stream leaving the distillation column.

4. The facility as claimed in claim 1, further comprising a liquid tank for storing the liquid stream leaving the distillation column.

5. The facility as claimed in claim 1, further comprising means for purifying the feed gas stream, placed upstream of the first membrane separation unit, and for at least partially removing an impurity chosen from water, hydrogen sulfide and volatile organic compounds.

6. The facility as claimed in claim 1, wherein the means for cooling the compressed first permeate to a temperature below −40° C. comprises a chiller and heat exchanger assembly.

7. A process for the membrane permeation treatment of a feed gas stream comprising at least methane and carbon dioxide, said process using the facility as defined in claim 1, and comprising:

a) a step of feeding the first membrane separation unit with the feed gas stream so as to produce a first retentate enriched in methane relative to the feed gas stream and a first permeate enriched in carbon dioxide relative to the feed gas stream;

b) a step of feeding the first retentate to the second membrane separation unit so as to produce a second retentate enriched in methane relative to the first retentate and a second permeate enriched in carbon dioxide relative to the first retentate;

c) a step of compressing the first permeate to a pressure of between 17 bar and 25 bar;

d) a step of cooling the compressed first permeate to a temperature below −40° C.;

e) a step of separating the cooled first permeate into a gas stream and a liquid stream in the distillation column;

f) a step of recycling the gas stream leaving the distillation column to the inlet of the first membrane separation unit;

g) a step of measuring the concentration of methane and/or carbon dioxide in the gas stream leaving the distillation column;

h) a step of comparing the concentration of methane and/or carbon dioxide measured by the measuring means with a target value, wherein the target value is between 10% $CH_4$ and 20% $CH_4$; and i) a step of adjusting the pressure and/or temperature of the first permeate as a function of the comparison made by the comparing means.

8. The process as claimed in claim 7, further comprising a step of compressing the feed gas stream to a pressure of between 8 bar and 16 bar upstream of the first membrane separation unit.

9. The process as claimed in claim 7, further comprising a step of evaporating the liquid stream leaving the distillation column.

10. The process as claimed in claim 7, further comprising a step of storing the liquid stream leaving the distillation column in a liquid tank.

11. The process as claimed in claim 7, further comprising a step of purifying the feed gas stream upstream of the first membrane separation unit, so as to at least partially remove an impurity chosen from water, hydrogen sulfide and volatile organic compounds.

12. The process as claimed in claim 7, wherein the feed gas stream is biogas.

* * * * *